(12) United States Patent
Kanada

(10) Patent No.: US 11,989,880 B2
(45) Date of Patent: May 21, 2024

(54) SIMILARITY DETERMINATION APPARATUS, SIMILARITY DETERMINATION METHOD, AND SIMILARITY DETERMINATION PROGRAM

(71) Applicant: FUJIFILM Corporation, Tokyo (JP)

(72) Inventor: Shoji Kanada, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 520 days.

(21) Appl. No.: 17/327,775

(22) Filed: May 24, 2021

(65) Prior Publication Data

US 2021/0279879 A1    Sep. 9, 2021

Related U.S. Application Data

(63) Continuation of application No. PCT/JP2019/041479, filed on Oct. 23, 2019.

(30) Foreign Application Priority Data

Nov. 27, 2018    (JP) .................................. 2018-221167

(51) Int. Cl.
*G06T 7/00*        (2017.01)
*G16H 30/40*       (2018.01)

(52) U.S. Cl.
CPC ........... *G06T 7/0014* (2013.01); *G16H 30/40* (2018.01); *G06T 2207/10028* (2013.01);
(Continued)

(58) Field of Classification Search
CPC ......... G06T 7/0014; G06T 2207/10028; G06T 2207/20021; G06T 2207/20081;
(Continued)

(56) References Cited

U.S. PATENT DOCUMENTS 8,605,978 B2    12/2013    Mizuno
10,055,543 B2    8/2018    Kozuka et al.
(Continued)

FOREIGN PATENT DOCUMENTS

CN    102208105    10/2011
CN    106164903    11/2016
(Continued)

OTHER PUBLICATIONS

"International Search Report (Form PCT/ISA/210) of PCT/JP2019/041479," dated Jan. 7, 2020, with English translation thereof, pp. 1-3.
(Continued)

*Primary Examiner* — Juan A Torres
(74) *Attorney, Agent, or Firm* — JCIPRNET

(57) ABSTRACT

A finding classification unit classifies each pixel of a first medical image into at least one finding. A feature amount calculation unit calculates a first feature amount for each finding. A similarity derivation unit derives a similarity between the first medical image and a second medical image on the basis of the first feature amount for each finding calculated in the first medical image and a second feature amount for each finding calculated in the second medical image. A region determination unit determines at least one important region including an important finding for deriving the similarity in the second medical image.

11 Claims, 15 Drawing Sheets

(52) U.S. Cl.
CPC ............... *G06T 2207/20021* (2013.01); *G06T 2207/20081* (2013.01); *G06T 2207/30004* (2013.01)

(58) Field of Classification Search
CPC . G06T 2207/30004; G06T 2207/10081; G06T 2207/10104; G06T 2207/20084; G06T 2207/30061; G06T 2207/30096; G16H 30/40; G16H 30/20; G16H 50/20; G16H 50/70; A61B 5/055; A61B 6/03
USPC ......................................................... 382/128
See application file for complete search history.

(56) References Cited

U.S. PATENT DOCUMENTS

| | | | |
|---|---|---|---|
| 10,839,511 B2 | 11/2020 | Oosawa | |
| 10,930,396 B2 | 2/2021 | Kanada | |
| 2008/0292194 A1* | 11/2008 | Schmidt | G06T 7/143 382/131 |
| 2009/0028403 A1* | 1/2009 | Bar-Aviv | G06T 7/0012 382/128 |

FOREIGN PATENT DOCUMENTS

| | | |
|---|---|---|
| CN | 106560827 | 4/2017 |
| JP | 2000342558 | 12/2000 |
| JP | 2001117936 | 4/2001 |
| JP | 2001155019 | 6/2001 |
| WO | 2018116727 | 6/2018 |

OTHER PUBLICATIONS

"Written Opinion of the International Searching Authority (Form PCT/ISA/237) of PCT/JP2019/041479," dated Jan. 7, 2020, with English translation thereof, pp. 1-7.

Adrien Depeursinge et al., "Case-based lung image categorization and retrieval for interstitial lung diseases: clinical workflows," Int J CARS, Jun. 2011, pp. 97-110.

Joseph Jacob et al., "Evaluation of computer-based computer tomography stratification against outcome models in connective tissue disease-related interstitial lung disease: a patient outcome study," BMC Medicine, Nov. 2016, pp. 1-13.

Tae Iwasawa, "Quantitative Evaluation of CT Images of Interstitial Pneumonia by Computer," with English abstract thereof, Japanese Journal of Tomography, vol. 41, Aug. 2014, pp. 1-11.

"Office Action of China Counterpart Application", issued on Dec. 20, 2023, with English translation thereof, p. 1-p. 20.

* cited by examiner

FIG. 4

| TYPE OF FINDING | EVALUATION VALUE |
|---|---|
| INFILTRATIVE SHADOW | 2.9 |
| GROUND-GLASS SHADOW | 7.6 |
| RETICULAR SHADOW | 8.5 (MAXIMUM) |
| BRONCHODILATATION | 3.2 |
| . . . | . . . |
| . . . | . . . |
| NORMAL LUNG | −7.1 |
| LOW ABSORPTION AREA (EMPHYSEMA) | −12.3 |

FIG. 5

| TYPE OF FINDING | VOLUME |
|---|---|
| GROUND-GLASS SHADOW | 20540 |
| INFILTRATIVE SHADOW | 11210 |
| LOW ABSORPTION AREA | 2890 |
| BRONCHODILATATION | 4030 |
| RETICULAR SHADOW | 9680 |
| CYST | 1430 |
| NORMAL LUNG | 157830 |

FIG. 6

| TYPE OF FINDING | WEIGHTING COEFFICIENT |
|---|---|
| INFILTRATIVE SHADOW | 0.28 |
| GROUND-GLASS SHADOW | 0.37 |
| RETICULAR SHADOW | 0.65 |
| BRONCHODILATATION | 0.09 |
| HONEYCOMB LUNG | 0.81 |
| PUNCTATE SHADOW | 0.12 |
| NORMAL LUNG | 0.23 |
| LOW ABSORPTION AREA (EMPHYSEMA) | 0.43 |

FIG. 7

| TYPE OF FINDING | SIMILARITY |
|---|---|
| INFILTRATIVE SHADOW | 0.20 |
| GROUND-GLASS SHADOW | 0.29 |
| RETICULAR SHADOW | 0.62 |
| BRONCHODILATATION | 0.02 |
| HONEYCOMB LUNG | 0.48 |
| PUNCTATE SHADOW | 0.09 |
| NORMAL LUNG | 0.19 |
| LOW ABSORPTION AREA (EMPHYSEMA) | 0.35 |

| CASE IMAGE | SIMILARITY |
|---|---|
| IMG0012.dcm | 0.87 |
| IMG0254.dcm | 0.77 |
| IMG0123.dcm | 0.54 |
| IMG0022.dcm | 0.52 |

SIMILARITY DETERMINATION APPARATUS, SIMILARITY DETERMINATION METHOD, AND SIMILARITY DETERMINATION PROGRAM

CROSS REFERENCE TO RELATED APPLICATIONS

The present application is a Continuation of PCT International Application No. PCT/JP2019/041479 filed on Oct. 23, 2019, which claims priority under 35 U.S.C. § 119(a) to Japanese Patent Application No. 2018-221167 filed on Nov. 27, 2018. Each of the above applications is hereby expressly incorporated by reference, in its entirety, into the present application.

BACKGROUND

Technical Field

The present disclosure relates to a similarity determination apparatus, a similarity determination method, and a similarity determination program that determine a similarity between two medical images.

Related Art

In recent years, with the progress of medical apparatuses, such as a computed tomography (CT) apparatus and a magnetic resonance imaging (MRI) apparatus, high-resolution three-dimensional images with higher quality have been used for image diagnosis.

On the other hand, in the medical field, a similar case search apparatus has been known which searches for past cases similar to an examination image, such as a CT image to be examined, on the basis of the examination image (for example, see "Case-based lung image categorization and retrieval for interstitial lung diseases: clinical workflows, Adrien Depeursinge et al., Int J CARS (2012) 7:97-110, Published online: 1 Jun. 2011"). The literature of Depeursinge et al. discloses a method which classifies a case image of the lung into a plurality of regions indicating a plurality of types of tissues or lesions (hereinafter, it is assumed that tissues or lesions are generically referred to as findings), registers the plurality of regions in a case database, similarly classifies an examination image of the lung into a plurality of regions indicating a plurality of types of findings, and searches for a case image similar to the examination image on the basis of the classification result of the findings for the examination image.

In addition, as a method for calculating the similarity between images, a method has been proposed which sets a plurality of partial regions in at least one of a plurality of images, determines the similarity between each of the set partial regions and each corresponding region in other images, and weights and adds the determined similarities for each partial region using a weighting coefficient set for each partial region to calculate the overall region similarity (see JP2000-342558A).

However, interstitial pneumonia is known as a lung disease. A method has been proposed which analyzes a CT image of a patient with interstitial pneumonia to classify and quantify lesions indicating specific findings, such as a honeycomb lung, a reticular shadow, and a cyst, included in the CT image (see "Evaluation of computer-based computer tomography stratification against outcome models in connective tissue disease-related interstitial lung disease: a patient outcome study, Joseph Jacobi et al., BMC Medicine (2016) 14:190, DOI 10.1186/s12916-016-0739-7" and "Quantitative Evaluation of CT Images of Interstitial Pneumonia by Computer, Iwasawa Tae, Japanese Journal of Tomography, vol. 41, No. 2, August 2014"). The method which analyzes a CT image and classifies and quantifies lesions makes it possible to easily determine the degree of lung disease. In addition, different colors are assigned to the classified and quantified regions and the regions are displayed, which makes it possible to easily diagnose how much a specific symptom region is included in the image.

Further, it is necessary to detect a structure in a three-dimensional image in order to extract a structure, such as an organ of interest, from a three-dimensional image such as a CT image. Here, a deep learning method has been proposed in order to classify the pixels of interest in an image into a plurality of classes. Deep learning is a machine learning method using a multi-layer neural network constructed by hierarchically connecting a plurality of processing layers.

In deep learning, in each layer of the multi-layer neural network, arithmetic processing is performed for a plurality of different arithmetic result data items obtained by the previous layer for input data, that is, data of the extraction result of feature amounts. Then, in the subsequent processing layers, arithmetic processing is further performed for the obtained data of the feature amounts to improve the recognition rate of the feature amounts, and the input data can be classified into a plurality of classes.

It is considered that the deep learning method is applied to the above-mentioned three-dimensional image to classify each pixel of the three-dimensional image into a plurality of classes. For example, in a case in which a plurality of types of structures included in a three-dimensional image are classified, deep learning is performed for a neural network, using a three-dimensional image as an input, such that the pixel to be processed in the three-dimensional image is classified into any one of a plurality of types of structures. The use of the neural network subjected to deep learning makes it possible to classify a pixel to be processed of the input three-dimensional image into any one of the plurality of types of structures.

The method disclosed in the literature of Depeursinge et al. can be used to search for a case image including a lesion similar to the lesion included in the organ, such as the lung, in the examination image and to display the searched case image. On the other hand, in a similar search using a three-dimensional image, it is difficult to represent the entire image with one image. Therefore, in a case in which a case image similar to the examination image is displayed, a slice image of a specific tomographic plane including a target organ is displayed. However, the displayed slice image of the case image does not always include the same lesion as the diagnosis target lesion included in the examination image. Therefore, it is necessary to sequentially switch and display the tomographic plane of the case image and to display the slice image including the lesion in order to check features, such as lesions, in the case image. It is difficult to quickly check the similarity between the displayed case image and the examination image only by sequentially displaying the slice image including the lesion. On the other hand, it is considered that the case image is displayed such that the organ included in the examination image is aligned with the organ included in the case image. However, the position of the tomographic plane including the lesion in the examination image and the position of the tomographic plane including a feature, such as the lesion, in the case image do not necessarily correspond to each other. Therefore, even in a case in which the alignment is performed, it is difficult to quickly check the similarity between the displayed case image and the examination image.

SUMMARY OF THE INVENTION

The present disclosure has been made in view of the above-mentioned problems, and an object of the present disclosure is to provide a technique that can quickly check features included in a case image in a case in which the case image similar to an examination image is displayed.

According to the present disclosure, there is provided a similarity determination apparatus that determines a similarity between a first three-dimensional medical image and a second three-dimensional medical image. The similarity determination apparatus comprises: a finding classification unit that classifies each pixel of the first medical image into at least one of a plurality of types of findings; a feature amount calculation unit that calculates a first feature amount for each finding classified in the first medical image; a similarity derivation unit that derives the similarity between the first medical image and the second medical image on the basis of the first feature amount for each finding calculated in the first medical image and a second feature amount for each finding calculated in advance in the second medical image; and a region determination unit that determines at least one important region including an important finding for deriving the similarity in the second medical image.

In addition, the similarity determination apparatus according to the present disclosure may further comprise a weighting coefficient setting unit that sets a weighting coefficient indicating a degree of weighting, which varies depending on a size of each finding, for each finding classified in the first medical image. The region determination unit may determine the important region on the basis of the weighting coefficient.

Further, in the similarity determination apparatus according to the present disclosure, the region determination unit may determine the important region on the basis of a similarity for each finding based on the first feature amount for each finding and the second feature amount for each finding.

Furthermore, the similarity determination apparatus according to the present disclosure may further comprise a region division unit that divides a target region of the first medical image into a plurality of regions. The feature amount calculation unit may calculate the first feature amount for each finding classified in the first medical image in each of the divided regions. The similarity derivation unit may derive a region similarity between the first medical image and the second medical image for each of the divided regions and may derive the similarity between the first medical image and the second medical image on the basis of a plurality of the region similarities. The region determination unit may determine the important region on the basis of the region similarities.

Moreover, the similarity determination apparatus according to the present disclosure may further comprise a search unit that searches for the second medical image similar to the first medical image as a similar medical image on the basis of similarities between the first medical image and a plurality of second medical images with reference to a case database in which the plurality of second medical images are registered and a second feature amounts for each of the plurality of second medical images are registered so as to be associated with the plurality of second medical images.

In addition, the similarity determination apparatus according to the present disclosure may further comprise a display control unit that displays a slice image including the important region in the similar medical image as a search result on a display unit.

Further, in the similarity determination apparatus according to the present disclosure, the display control unit may display a slice image which passes through a center of gravity of one important region in the similar medical image as a search result on the display unit.

Furthermore, in the similarity determination apparatus according to the present disclosure, the display control unit may display a slice image in which an area of one important region is maximized in the similar medical image as a search result on the display unit.

Moreover, the similarity determination apparatus according to the present disclosure may further comprise a display control unit that three-dimensionally displays the similar medical image in which the important region is highlighted as a search result on a display unit.

According to the present disclosure, there is provided a similarity determination method that determines a similarity between a first three-dimensional medical image and a second three-dimensional medical image. The similarity determination method comprises: classifying each pixel of the first medical image into at least one of a plurality of types of findings; calculating a first feature amount for each finding classified in the first medical image; deriving the similarity between the first medical image and the second medical image on the basis of the first feature amount for each finding calculated in the first medical image and a second feature amount for each finding calculated in advance in the second medical image; and determining at least one important region including an important finding for deriving the similarity in the second medical image.

In addition, a program that causes a computer to perform the similarity determination method according to the present disclosure may be provided.

Another similarity determination apparatus according to the present disclosure comprises a memory that stores commands to cause a computer to perform a process of determining a similarity between a first medical image and a second medical image and a processor configured to execute the stored commands. The processor performs a process of: classifying each pixel of the first medical image into at least one of a plurality of types of findings; calculating a first feature amount for each finding classified in the first medical image; deriving the similarity between the first medical image and the second medical image on the basis of the first feature amount for each finding calculated in the first medical image and a second feature amount for each finding calculated in advance in the second medical image; and determining at least one important region including an important finding for deriving the similarity in the second medical image.

According to the present disclosure, in a case in which a case image similar to the examination image is displayed, it is possible to quickly check the features included in the case image.

BRIEF DESCRIPTION OF THE DRAWINGS

FIG. 4 is a diagram illustrating an evaluation value corresponding to the type of finding for a central pixel of a certain region of interest.

FIG. 5 is a diagram illustrating the calculation results of the volumes of findings.

FIG. 6 is a diagram illustrating a relationship between the type of finding and a weighting coefficient.

FIG. 7 is a diagram illustrating a relationship between the type of finding and a similarity.

DETAILED DESCRIPTION

Figure 1:
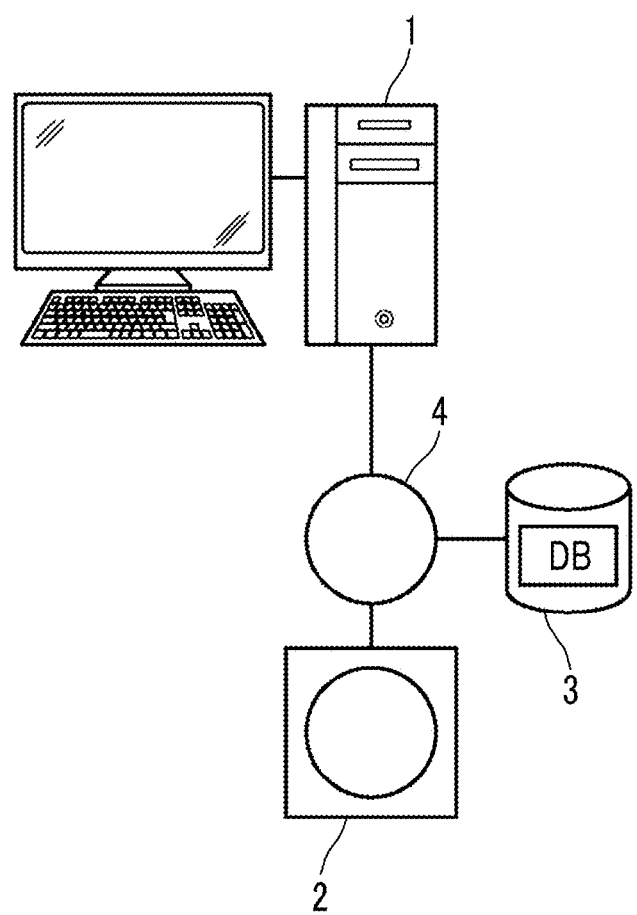
FIG. 1 is a hardware configuration diagram illustrating the outline of a diagnosis support system to which a similarity determination apparatus according to a first embodiment of the present disclosure is applied.

Hereinafter, embodiments of the present disclosure will be described with reference to the drawings. FIG. 1 is a hardware configuration diagram illustrating the outline of a diagnosis support system to which a similarity determination apparatus according to a first embodiment of the present disclosure is applied. As illustrated in FIG. 1, in the diagnosis support system, a similarity determination apparatus 1 according to this embodiment, a three-dimensional imaging apparatus 2, and an image storage server 3 are connected so as to communicate with each other through a network 4.

The three-dimensional imaging apparatus 2 is an apparatus that captures an image of a diagnosis target part of a subject to generate a three-dimensional image indicating the part and is, specifically, a CT apparatus, an MM apparatus, a positron emission tomography (PET) apparatus, and the like. The three-dimensional image which consists of a plurality of slice images and has been generated by the three-dimensional imaging apparatus 2 is transmitted to the image storage server 3 and is then stored therein. In addition, in this embodiment, the diagnosis target part of a patient that is the subject is the lung, and the three-dimensional imaging apparatus 2 is a CT apparatus and generates a CT image of the chest including the lung of the subject as the three-dimensional image.

The image storage server 3 is a computer that stores and manages various types of data and comprises a high-capacity external storage device and database management software. The image storage server 3 performs communication with other apparatuses through the wired or wireless network 4 to transmit and receive, for example, image data. Specifically, the image storage server 3 acquires various types of data including the image data of the three-dimensional image generated by the three-dimensional imaging apparatus 2 through the network, stores the acquired data in a recording medium, such as a high-capacity external storage device, and manages the data. In addition, the storage format of the image data and the communication between the apparatuses through the network 4 are based on a protocol such as Digital Imaging and Communication in Medicine (DICOM). In this embodiment, it is assumed that the image storage server 3 stores three-dimensional images to be examined (hereinafter, referred to as examination images) and a case database DB having case images registered therein. The case database DB will be described below. In addition, in this embodiment, the examination image is a three-dimensional image consisting of one or more slice images (hereinafter, referred to as examination slice images). The case image is also a three-dimensional image consisting of one or more slice images (hereinafter, referred to as case slice images). Further, the examination image corresponds to a first medical image and the case image corresponds to a second medical image.

The similarity determination apparatus 1 is configured by installing a similarity determination program according to the present disclosure in one computer. The computer may be a workstation or a personal computer that is directly operated by a doctor who makes a diagnosis or may be a server computer that is connected to them through the network. The similarity determination program is recorded on a recording medium, such as a digital versatile disc (DVD) or a compact disc read only memory (CD-ROM), is distributed, and is installed in the computer from the recording medium. Alternatively, the similarity determination program is stored in a storage device of a server computer connected to the network, or is stored in a network storage so as to be accessed from the outside, is downloaded to the computer used by the doctor on request, and is then installed in the computer.

Figure 2:
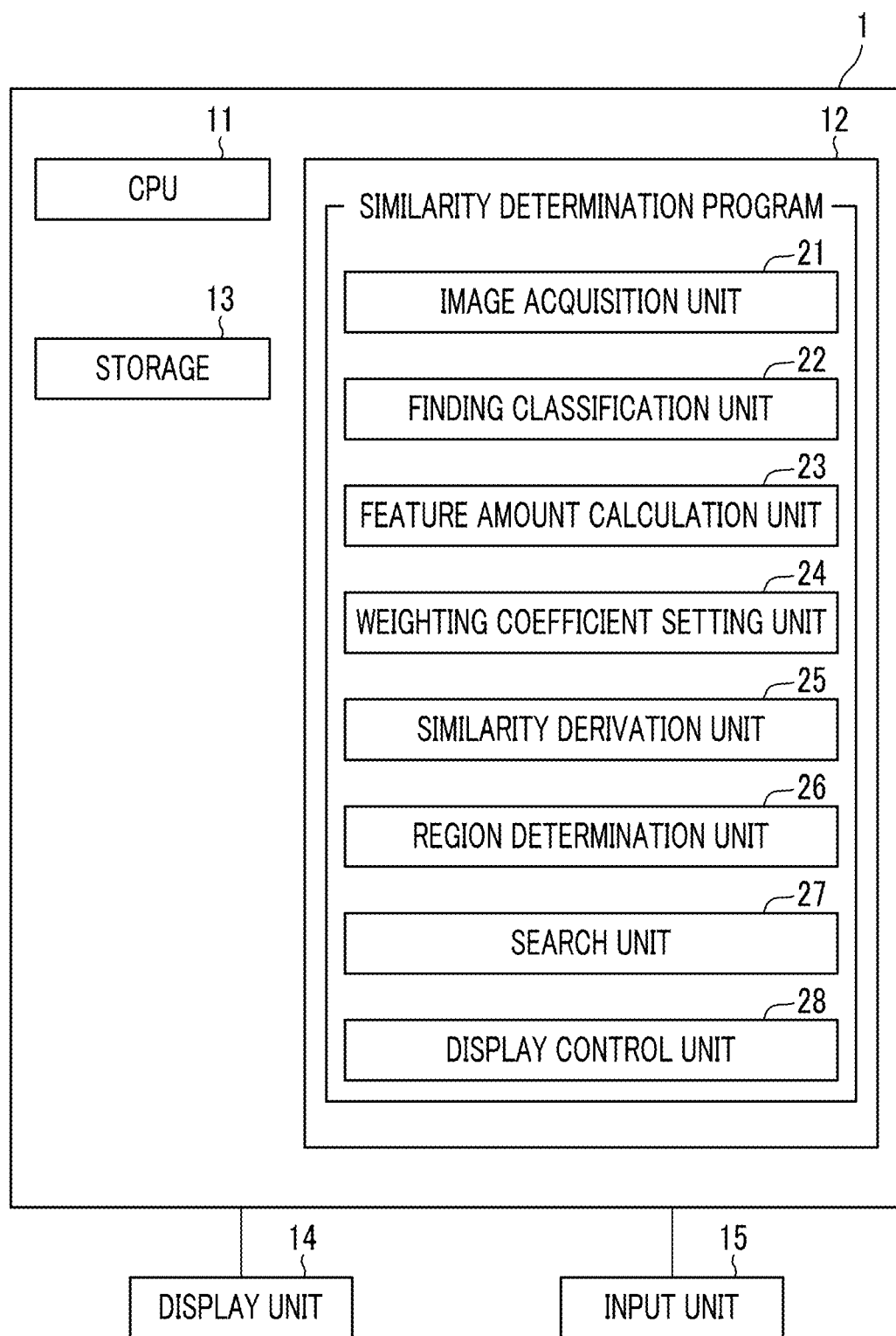
FIG. 2 is a block diagram schematically illustrating the configuration of the similarity determination apparatus according to the first embodiment.

FIG. 2 is a diagram schematically illustrating the configuration of the similarity determination apparatus according to the first embodiment of the present disclosure which is implemented by installing the similarity determination program according to the first embodiment in the computer. As illustrated in FIG. 2, the similarity determination apparatus 1 has the configuration of a standard workstation and comprises a central processing unit (CPU) 11, a memory 12, and a storage 13. In addition, a display unit 14 consisting of, for example, a liquid crystal display and an input unit 15 consisting of, for example, a keyboard and a mouse are connected to the similarity determination apparatus 1.

The storage 13 consists of, for example, a hard disk drive and a solid state drive (SSD). The storage 13 stores various kinds of information which include the examination image of the subject and information required for processes and are acquired from the image storage server 3 through the network 4.

Further, the memory 12 stores the similarity determination program. The similarity determination program defines the following processes as the processes performed by the CPU 11: an image acquisition process that acquires an examination image to be examined; a finding classification process that classifies each pixel of the examination image into at least one of a plurality of types of findings; a feature amount calculation process that calculates a first feature amount for each finding classified in the examination image; a weighting coefficient setting process that sets a weighting coefficient indicating the degree of weighting, which varies depending on the size of each finding, for each finding classified in the examination image; a similarity derivation process that performs a weighting operation for the first feature amount for each finding calculated in the examination image and a second feature amount for each finding calculated in advance in a case image on the basis of the weighting coefficient to derive the similarity between the examination image and the case image; a region determination process that determines at least one important region including an important finding for deriving the similarity in the case image; a search process that searches for a case image similar to the examination image on the basis of the derived similarity; and a display control process that displays search results on the display unit 14.

Then, the CPU 11 performs these processes according to the program such that the computer functions as an image acquisition unit 21, a finding classification unit 22, a feature amount calculation unit 23, a weighting coefficient setting unit 24, a similarity derivation unit 25, a region determination unit 26, a search unit 27, and a display control unit 28.

The image acquisition unit 21 acquires an examination image V0 of a subject to be examined. Further, in a case in which the examination image V0 has already been stored in the storage 13, the image acquisition unit 21 may acquire the examination image V0 from the storage 13.

The finding classification unit 22 classifies each pixel of a lung region included in the examination image V0 into at least one of a plurality of types of findings. Specifically, the finding classification unit 22 calculates a plurality of evaluation values indicating the possibility that each pixel of the lung region included in the examination image V0 will be each of a plurality of types of tissues or lesions (for example, findings) and classifies each pixel of the examination image V0 into at least one of the plurality of types of findings on the basis of the plurality of evaluation values. In this embodiment, it is assumed that the finding classification unit 22 classifies each pixel of the examination image V0 into one finding.

The finding classification unit 22 according to this embodiment includes a discriminator which consists of a multi-layer neural network generated by deep learning that is one kind of machine learning and specifies the type of finding, to which each pixel of the examination image V0 belongs, using the discriminator. In addition, a machine learning method is not limited to the deep learning and other methods including a support vector machine may be used.

In each layer of the multi-layer neural network, arithmetic processing is performed for data of a plurality of different feature amounts obtained by the previous layer, using various kernels. Then, in the subsequent layers, arithmetic processing can be further performed for the data of the feature amounts obtained by the arithmetic processing to improve the recognition rate of the feature amounts and the input data can be classified into a plurality of classes.

Further, in this embodiment, the multi-layer neural network receives the examination image V0 as an input and outputs the classification result of the lung region into a plurality of types of findings. However, the multi-layer neural network may be configured such that it receives each of a plurality of examination slice images forming the examination image V0 as an input and outputs the classification result of the lung region into a plurality of types of findings.

Figure 3:
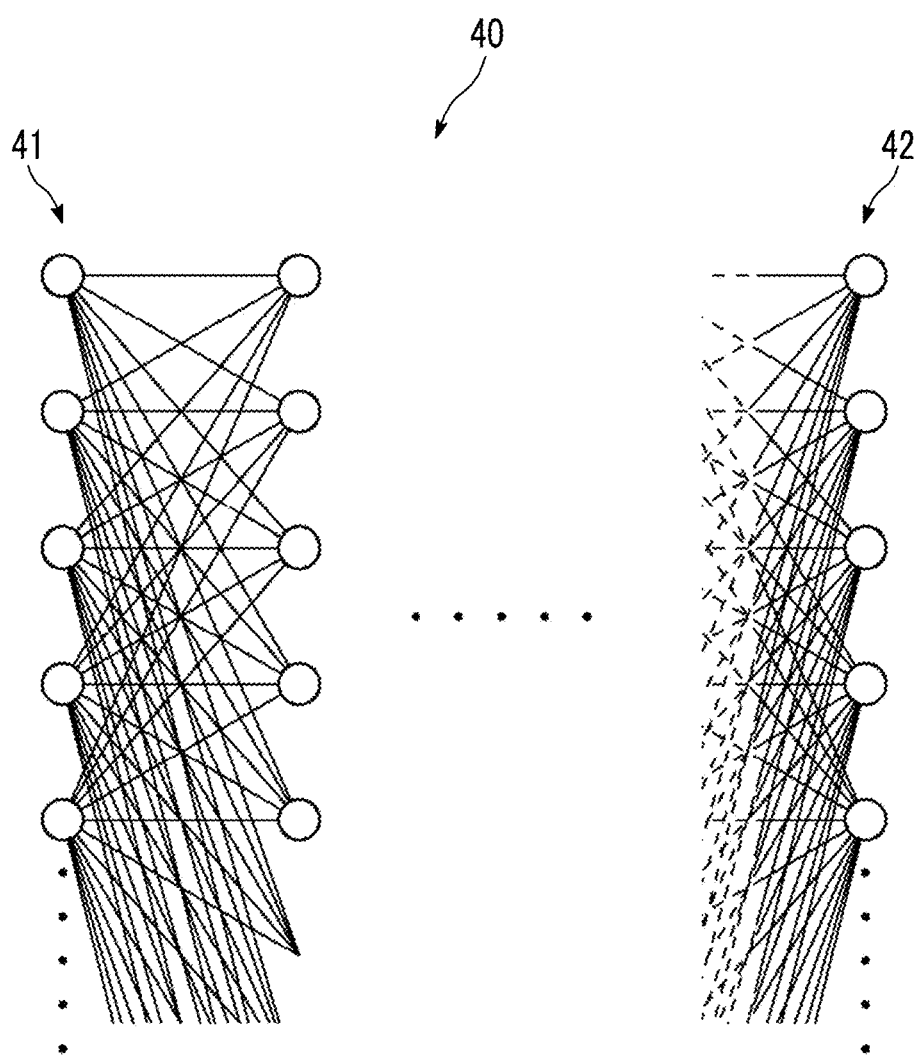
FIG. 3 is a diagram illustrating an example of a multi-layer neural network.

FIG. 3 is a diagram illustrating an example of the multi-layer neural network. As illustrated in FIG. 3, a multi-layer neural network 40 consists of a plurality of layers including an input layer 41 and an output layer 42. In this embodiment, learning is performed such that the lung region included in the examination image V0 is classified into a plurality of findings, such as an infiltrative shadow, a mass shadow, a ground-glass shadow, a centrilobular nodular shadow, a non-centrilobular nodular shadow, a reticular shadow, a linear shadow, interlobular septal thickening, a honeycomb lung, a cyst, a low absorption area (emphysema), emphysema tendency, a cavity, pleural thickening, pleural effusion, bronchodilatation, traction bronchiectasis, artery, a normal lung, a chest wall, and mediastinum. In addition, the types of findings are not limited thereto and may be more or less than these findings.

In this embodiment, the multi-layer neural network 40 learns these findings using a large amount of training data such as millions of training data items. In the learning, a region of interest with a predetermined size (for example, 1.5 cm×1.5 cm) is cut out from a tomographic image in which the types of findings have been known. Then, the region of interest is used as the training data. Then, the training data is input to the multi-layer neural network 40 and the result of a finding type classification process (hereinafter, referred to as a classification result) is output from the multi-layer neural network 40. Then, the output result is compared with the training data, and the weight of the connection between the layers of units (represented by circles in FIG. 3) included in each layer of the multi-layer neural network 40 is corrected from the output side to the input side according to whether the answer is correct or incorrect. The correction of the weight of the connection is repeated using a large amount of training data a predetermined number of times or until the accuracy rate of the output classification result reaches 100%, and the learning ends.

Further, in a case in which the input image is the examination slice image, in the learning of the multi-layer neural network 40, a two-dimensional region normalized to a predetermined size (for example, 1.5 cm×1.5 cm) is cut out from a slice image forming a three-dimensional image in which a lesion has been known, and the image of the cut-out two-dimensional region is used as the training data.

First, the finding classification unit 22 extracts a lung region that is a target region from the examination image V0 for classification. Any method, such as a method that creates a histogram of the signal value of each pixel of the examination image V0 and performs threshold processing for the lung to extract the lung region or a region growing method based on a seed point indicating the lung, can be used as a method of extracting the lung region. In addition, a discriminator which has been subjected to machine learning so as to extract the lung region may be used.

In a case in which the finding classification process is performed, the finding classification unit 22 sequentially cuts out the region of interest having the same size as the training data from the lung region of the examination image V0 and inputs the region of interest to the discriminator consisting of the multi-layer neural network 40. Then, for a central pixel of the cut-out region of interest, an evaluation value corresponding to each classification of the findings is output. In addition, the evaluation value corresponding to each classification is an evaluation value indicating the possibility that the central pixel will belong to each classification. As the evaluation value becomes larger, the possibility that the central pixel will belong to the classification becomes higher.

FIG. 4 is a diagram illustrating an evaluation value corresponding to the type of finding for a central pixel of a certain region of interest. In addition, FIG. 4 illustrates evaluation values for some findings for simplicity of description. In this embodiment, the discriminator classifies the central pixel of the region of interest into a finding with the maximum evaluation value among a plurality of findings. For example, in a case in which the evaluation values illustrated in FIG. 4 are acquired, the central pixel of the region of interest has the highest possibility of being the reticular shadow and has the second highest possibility of being the ground-glass shadow. On the contrary, there is almost no possibility that the central pixel will be the normal lung or the low absorption area. Therefore, in a case in which the evaluation values illustrated in FIG. 4 are acquired, the central pixel of the region of interest is classified into the reticular shadow having a maximum evaluation value of 8.5 by the finding classification process. In this way, all of the pixels of the lung region included in the examination image V0 are classified into any of a plurality of types of findings.

The finding classification unit 22 sequentially cuts out the same voxel region as the training data from the extracted lung region and sequentially inputs the cut-out voxel region to the discriminator of the multi-layer neural network 40 which has been trained as described above. Then, for the central pixel of the cut-out region, a plurality of evaluation values for each of a plurality of types of lesion regions are output. The finding classification unit 22 classifies the central pixel of the region input to the multi-layer neural network 40 into a finding with the maximum evaluation value among the plurality of evaluation values and generates the classification result of the findings. In this way, all of the pixels of the lung region included in the examination image V0 are classified into any of a plurality of types of findings.

The feature amount calculation unit 23 calculates a feature amount for each of the findings classified in the examination image V0. Specifically, the feature amount calculation unit 23 calculates, as the feature amount, at least one of the size of a region for each finding, average density for each finding, the variance of density for each finding, the number of regions for each finding, or the average size of the region for each finding. In addition, it is assumed that the feature amount calculated for the examination image V0 is referred to as a first feature amount. Further, for example, the size of the region for each finding, the number of regions for each finding, and the average size of the region for each finding are size feature amounts. The volume of the region for each finding can be used as the size of the region for each finding.

In addition, a file name, evaluation values for a plurality of findings in each pixel, and feature amounts for each finding are registered for each of a plurality of case images in the above-described case database DB. It is assumed that the feature amount registered in the case database DB for the case image is referred to as a second feature amount. The first feature amount and the second feature amount are normalized to values that are equal to or greater than 0 and equal to or less than 1. In a case in which evaluation values for a plurality of findings in each pixel and feature amounts for each finding are acquired for the examination image V0, the examination image V0 is registered as a new case image in the case database DB. In this case, the evaluation value and the first feature amount for the examination image V0 are registered as the evaluation value and the second feature amount for the new case image in the case database DB.

The weighting coefficient setting unit 24 sets a weighting coefficient indicating the degree of weighting, which varies depending on the size of each finding, for each finding into which each pixel of the examination image V0 has been classified. The weighting coefficient is used for a weighting operation that is performed for the first feature amount for each finding calculated in the examination image V0 and the second feature amount for each finding which has been calculated in the case image in advance prior to the similarity derivation process which will be described below, that is, has been registered in the case database DB in the similarity derivation process. Further, in this embodiment, the weighting coefficient set by the weighting coefficient setting unit 24 is also used in a case in which the region determination unit 26 determines the important region.

Here, medical images have various features. Therefore, in a case in which the feature amounts are not appropriately weighted considering the importance of the feature amounts from the viewpoint of the medical images, the magnitude of the difference between the feature amounts does not correspond to the magnitude of the difference between the medical images, and the similarity deviates from the medical sense. Therefore, in a case in which the feature amounts are not appropriately weighted, in the search of a case image similar to the examination image V0, the search results are likely to be arranged in the order of inappropriate similarities.

In addition, in a case in which the same findings having almost the same size are present in the examination image V0 and the case image, two images are medically similar to each other. Further, as a finding region becomes larger, the finding becomes more important in diagnosis. Therefore, the size of the finding is extremely important in determining the similarity between the images.

The findings include important findings, such as punctate shadows, that indicate the features of the initial state of a disease even in a case in which they have a small size. Further, in a case in which lung emphysema progresses due to aging, a slightly low absorption state occurs in the lung. The finding of low absorption is less important because it is more common in older patients. The low absorption findings in elderly persons are not very important even though they have a large size.

Therefore, in a case in which the finding of the punctate shadow and the low absorption finding in an elderly person are equally determined, a subtle difference in the low absorption area of a large region is larger than a difference in the punctate shadow. As a result, the similarity between the punctate shadows is buried in the similarity between the low absorption areas, and it is difficult to search for a case image including a case of the punctate shadow that is medically important.

For this reason, in this embodiment, the weighting coefficient setting unit 24 sets the weighting coefficient indicating the degree of weighting, which varies depending on the size of each finding, for each of a plurality of findings. The size feature amount included in the first feature amount calculated by the feature amount calculation unit 23 can be used as the size of the finding. Specifically, the volume of the finding can be used. Here, the volume of the finding can be calculated by multiplying the number of pixels of each finding included in the three-dimensional examination image V0 by the volume per voxel in the examination image V0. FIG. 5 illustrates the calculation results of the volume of the findings. In FIG. 5, the unit of volume is cubic millimeters. The size of the lung varies depending on the patient. Therefore, it is preferable to use, as the size of the finding, finding occupancy (=the volume of the finding/the volume of the lung) obtained by normalizing the volume of the finding with the volume of the organ, that is, the volume of the lung. In this embodiment, it is assumed that finding occupancy is used as the size of the finding. In addition, the finding occupancy may be included as the size feature amount in the first feature amount. In this case, the feature amount calculation unit 23 may calculate the finding occupancy.

For each finding of the examination image V0, the weighting coefficient setting unit 24 sets a weighting coefficient Wi for each finding, using the following Expression (1). In Expression (1), i is the type of finding, and fi is a function that has the finding occupancy Pvi of each finding in the examination image V0 as a parameter.

$$Wi = fi(Pvi) \quad (1)$$

Here, as illustrated in FIG. 5, the number of digits in the value of the volume is different between a finding with a large size and a finding with a small size. Therefore, it is preferable to reduce the dimensions, for example, by converting the finding occupancy, which is three-dimensional information, into a two-dimensional finding occupancy using the function fi. In this case, the difference in the size of the finding is matched with the perception of the doctor. For this reason, as described above, it is preferable to nonlinearly convert a finding which has a small size, but is important using the function fi in order to increase the importance of the finding. Therefore, in this embodiment, the function fi is set as represented by the following Expression (2).

$$fi = a \cdot (b \cdot X + (1-b) \cdot X^c) \quad (2)$$

Further, in Expression (2), a is a constant that determines a difference in the overall importance of each finding. c is a constant that has a value of 1 or less and determines the effect of emphasizing a finding with a small size. b is a constant that determines the degree of the effect by the constant c. In addition, $X = (Pvi)^{2/3}$ is established. The finding occupancy Pvi is multiplied by ⅔ to be converted from a three-dimensional value to a two-dimensional value.

The weighting coefficient setting unit 24 sets the function represented by Expression (2) for each finding and applies the function to Expression (1) to set the weighting coefficient Wi for each of the plurality of types of findings.

The similarity derivation unit 25 performs a weighting operation for the first feature amount for each finding calculated in the examination image V0 and the second feature amount for each finding calculated in advance in the case image on the basis of the weighting coefficient Wi set by the weighting coefficient setting unit 24 to derive the similarity between the examination image V0 and the case image. In addition, the similarity derivation unit 25 derives the similarities between the examination image V0 and all of the case images registered in the case database DB.

For the derivation, the similarity derivation unit 25 normalizes the first feature amount calculated for the examination image V0 to a value that is equal to or greater than 0 and equal to or less than 1. Then, the similarity derivation unit 25 calculates, as a feature amount difference Ddi, a difference in the distance between the first feature amount and the second feature amount of the case image for each finding, as represented by the following Expression (3). Further, in Expression (3), k indicates the type of feature amount, Tvk indicates the first feature amount for each type in the examination image V0, and Tck indicates the second feature amount for each type in the case image. Furthermore, the first feature amount and the second feature amount whose difference is calculated are the same type. In addition, in Expression (3), Σ indicates the calculation of the sum of $(Tvk-Tck)^2$ for all of the types of feature amounts. Further, since the first feature amount and the second feature amount are normalized to a value that is equal to or greater than 0 and equal to or less than 1, the feature amount difference Ddi is also a value that is equal to or greater than 0 and equal to or less than 1. Furthermore, in a case in which the first feature amount Tvk is equal to the second feature amount Tck, the feature amount difference Ddi is 0. Moreover, instead of the difference in the distance between the first feature amount and the second feature amount, for example, the absolute value of the difference between the first feature amount and the second feature amount may be used.

$$Ddi = \sqrt{(\Sigma(Tvk-Tck)^2)} \quad (3)$$

Then, the similarity derivation unit 25 calculates a similarity S0 between the examination image V0 and the case image, using the weighting coefficient Wi, as represented by the following Expression (4). That is, the similarity derivation unit 25 multiplies the feature amount difference Ddi by the weighting coefficient Wi for each finding and adds the multiplication results for all of the findings to calculate the similarity S0. In addition, in a case in which the similarity S0 is calculated using Expression (4), the similarity between the examination image V0 and the case image becomes higher as the distance between the first feature amount and the second feature amount becomes shorter. Therefore, a negative sign is given to Expression (4) such that, as the similarity between the examination image V0 and the case image becomes higher, the value of the similarity S0 becomes larger.

$$S0 = -\Sigma(Wi \times Ddi) \quad (4)$$

In contrast, in the calculation of the similarity by Expression (4), in a case in which the same findings have the same size, the similarity is 0. However, in a case in which the same lesions are compared with each other, the fact is that, as the size of the lesions becomes larger, the similarity between the lesions becomes higher. In a case in which the similarity is calculated by Expression (4), there is no difference between a case in which findings having a relatively large size have the same feature amount and a case in which findings having a relatively small size have the same feature amount, and it is difficult to reflect the fact that, as the size of the lesions becomes larger, the similarity between the lesions becomes higher.

For this reason, for the same finding included in the examination image V0 and the case image, only the difference in size therebetween is not treated, and it is preferable that the similarity becomes higher as the sizes become more similar to each other. Therefore, in this embodiment, the similarity derivation unit 25 further calculates a difference Dsi between the sizes of the findings in the examination image V0 and the case image, using the following Expression (5). Further, in Expression (5), Pvi indicates the finding occupancy of a finding i in the examination image V0, and Pci indicates the finding occupancy of the finding i in the case image.

$$Dsi = 1 - |Pvi - Pci|/(Pvi + Pci) \quad (5)$$

Therefore, it is preferable that the similarity derivation unit 25 calculates a similarity S1 between the examination image V0 and the case image using the following Expression (6). Here, Ddi is a value that becomes smaller as the similarity between the feature amounts of the findings in the examination image V0 and the case image becomes higher, and Dsi is a value that becomes larger as the sizes of the findings in the examination image V0 and the case image become more similar to each other. Therefore, it is possible to calculate the similarity that becomes higher as the examination image V0 and the case image become more similar to each other using Expression (6), considering the sizes of the same findings.

$$S1 = \Sigma(Wi \times (Dsi - Ddi)) \quad (6)$$

In a case in which the similarity S1 is calculated by Expression (6), the maximum value of the similarity S1 varies depending on the examination image V0. Therefore, it is preferable to normalize the similarity S1 under the condition that the similarity S1 between the examination image V0 and the case image is at its maximum, that is, the condition that there is no difference between the examination image V0 and the case image. Expression (7) is obtained by normalizing the similarity S1 calculated by Expression (6) under the condition that the similarity S1 between the examination image V0 and the case image is at its maximum. In Expression (7), S2 indicates the normalized similarity.

$$S2 = S1/\Sigma Wi = \Sigma(Wi \times (Dsi - Ddi))/\Sigma Wi \quad (7)$$

In addition, in a case in which the similarity is calculated by Expression (4), it is preferable to normalize the similarity S0. Expression (8) is obtained by normalizing Expression (4) under the condition that the similarity S0 between the examination image V0 and the case image is at its maximum. In Expression (8), S3 indicates the normalized similarity.

$$S3 = S0/\Sigma Wi = \Sigma(Wi \times Dsi)/\Sigma Wi \quad (8)$$

The region determination unit 26 determines at least one important region including an important finding for deriving the similarity in the case image. In this embodiment, the important region is determined on the basis of the weighting coefficient Wi for each finding set by the weighting coefficient setting unit 24. Specifically, the region of the finding for which the weighting coefficient Wi set on the basis of Expression (1) is equal to or greater than a predetermined threshold value Th1 is determined as the important region.

FIG. 6 is a diagram illustrating the relationship between the type of finding and the weighting coefficient. Here, in a case in which the threshold value Th1 is 0.7, the finding for which the weighting coefficient is equal to or greater than 0.7 is the honeycomb lung. Therefore, the region of the honeycomb lung is determined as the important region.

In addition, a method for determining the important region on the basis of the weighting coefficient Wi is not limited to the above. For example, the threshold value Th1 may be determined on the basis of a maximum weighting coefficient Wmax among the weighting coefficients Wi. For example, a value obtained by multiplying the maximum weighting coefficient Wmax by 0.75 may be set as the threshold value Th1. In FIG. 6, the maximum weighting coefficient Wmax is 0.81 for the honeycomb lung. In this case, the threshold value Th1 is 0.81×0.75≈0.61. Therefore, the regions of the reticular shadow (weighting coefficient of 0.65) and the honeycomb lung (weighting coefficient of 0.81) for which the weighting coefficient Wi is equal to or greater than 0.61 are determined as the important regions.

In addition, the region determination unit 26 may determine the important region on the basis of the similarity derived by the similarity derivation unit 25. Specifically, the important region may be determined on the basis of the similarity for each finding based on the first feature amount for each finding and the second feature amount for each finding. For example, in a case in which the similarity is derived by Expression (3), the region of the finding in which the feature amount difference Ddi for each finding is equal to or less than a predetermined threshold value Th2 may be determined as the important region. Further, in a case in which the similarity is derived by Expression (6), the region of the finding in which (Dsi-Ddi) is equal to or greater than a predetermined threshold value Th3 may be determined as the important region.

FIG. 7 is a diagram illustrating the relationship between the type of finding and the similarity in a case in which the similarity is derived by Expression (6). Here, in a case in which the threshold value Th3 is 0.5, the finding for which the similarity is equal to or greater than 0.5 is the reticular shadow. Therefore, the region of the reticular shadow is determined as the important region.

In addition, a method for determining the important region on the basis of the similarity is not limited to the above. For example, the threshold values Th2 and Th3 may be determined on the basis of the maximum similarity. For example, a value obtained by multiplying the maximum similarity by 0.75 may be set as the threshold values Th2 and Th3. In FIG. 7, the maximum similarity is 0.62 for the reticular shadow. In this case, the threshold value Th3 is 0.62×0.75≈0.47. Therefore, the regions of the reticular shadow (similarity of 0.62) and the honeycomb lung (similarity of 0.48) for which the similarity is equal to or greater than 0.47 are determined as the important regions.

The search unit 27 performs a search process of searching for a case image similar to the examination image V0 as a similar case image from the case database DB on the basis of the similarity S2. First, the case database DB will be described.

A plurality of case images, each of which consists of one or more case slice images, are registered in the case database DB. Specifically, as the classification result of the findings for each of the plurality of case images, the feature amount (that is, the second feature amount) is registered so as to be associated with each of the plurality of case images. In this embodiment, in a case in which a new examination image V0 is acquired, the examination image V0 is registered as a new case image in the case database DB.

Figure 8:
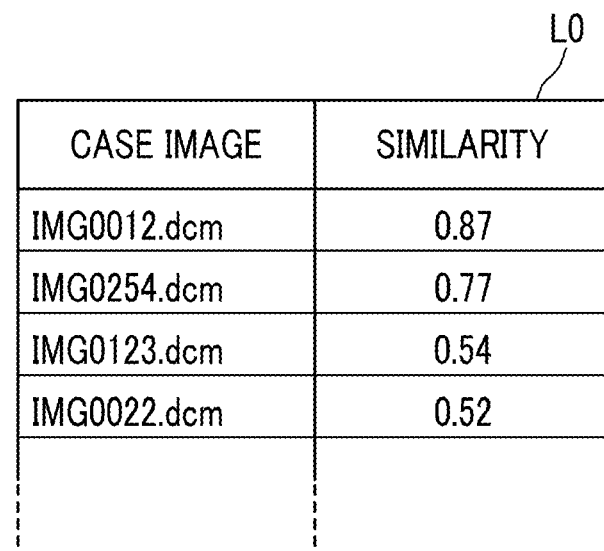
FIG. 8 is a diagram illustrating a search result list.

The search unit 27 searches for a case image similar to the examination image V0 as the similar case image on the basis of the similarities S2 between the examination image V0 and all of the case images registered in the case database DB. Specifically, the search unit 27 sorts the case images in descending order of the similarity S2 to create a search result list. FIG. 8 is a diagram illustrating the search result list. As illustrated in FIG. 8, the case images registered in the case database DB are sorted in descending order of the similarity S2 in a search result list L0. Then, the search unit 27 extracts a predetermined number of top case images sorted in the search result list L0 as the similar case images from the case database DB. In addition, the similar case image corresponds to a similar medical image.

Figure 9:
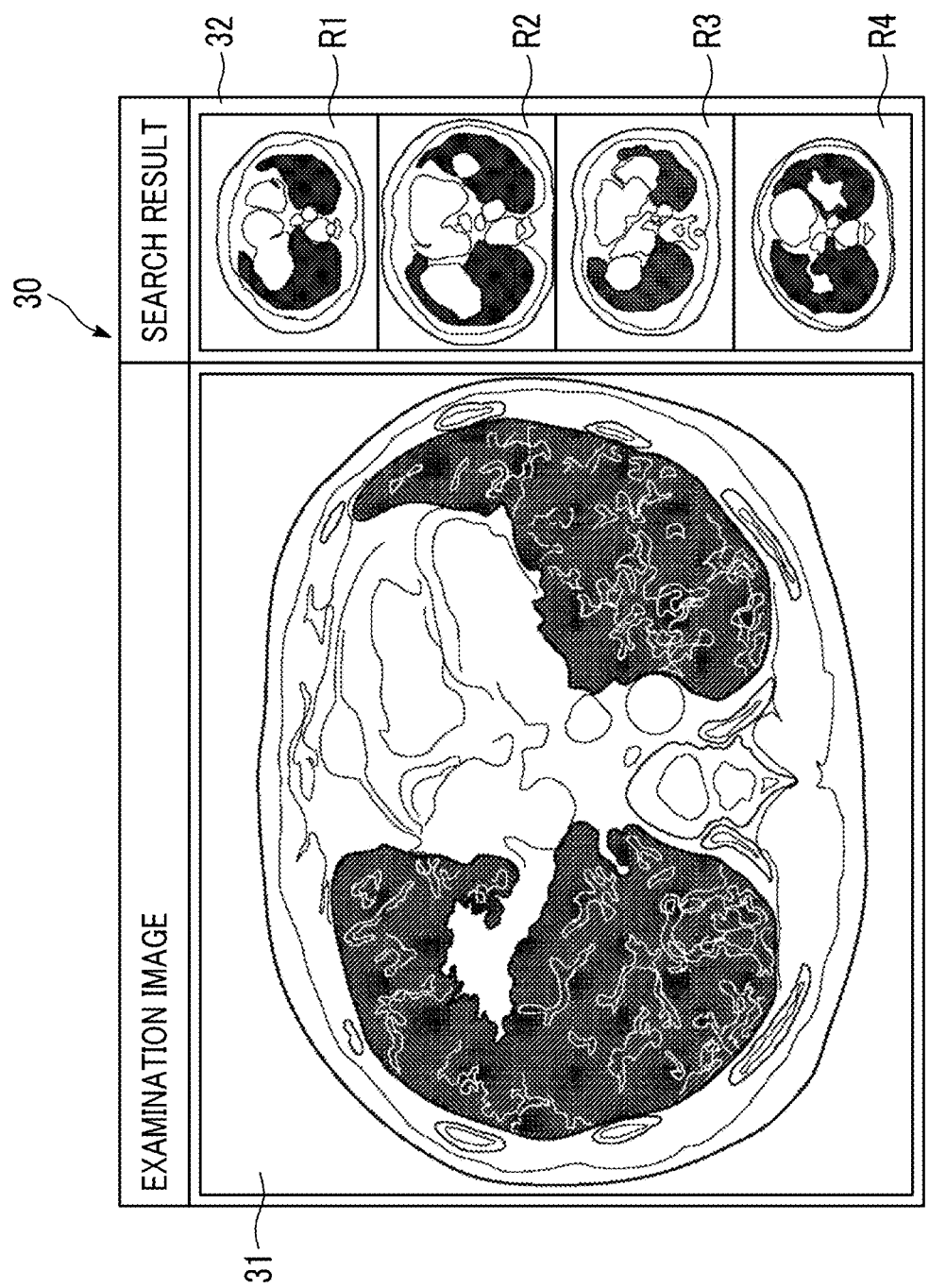
FIG. 9 is a diagram illustrating a search result display screen.

The display control unit 28 displays the search results of the search unit 27 on the display unit 14. FIG. 9 is a diagram illustrating a search result display screen. As illustrated in FIG. 9, the display screen 30 has an examination image display region 31 and a search result display region 32. An examination slice image of a desired axial cross section in the examination image is displayed in the examination image display region 31. Similar case images R1 to R4 are displayed in the search result display region 32. Specifically, the case slice images of the axial cross sections including an important region in the similar case images R1 to R4 are displayed as the search results. Further, in the state illustrated in FIG. 9, the desired similar case images R1 to R4 are selected in the search result display region 32, and the tomographic plane of the selected similar case image can be switched and displayed by an operation from the input unit 15.

Figure 10:
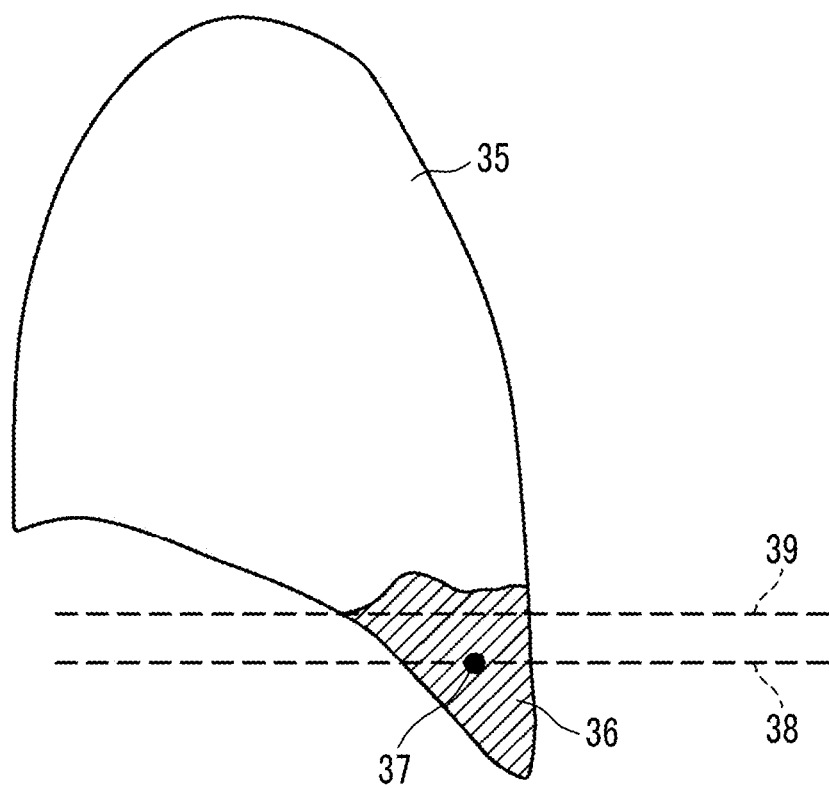
FIG. 10 is a diagram illustrating a tomographic plane including an important region.

Here, since the important region is a three-dimensional region, it extends in the axial direction. FIG. 10 is a diagram illustrating the extension of the important region in the axial direction. As illustrated in FIG. 10, an important region 36 determined in a lung region 35 extends in the axial direction. In this embodiment, the case slice image of an axial cross section 38 passing through the center of gravity 37 of the important region 36 in the similar case image is displayed as the search result. In addition, in a case in which a plurality of important regions are determined by the region determination unit 26, the case slice image of an axial cross section passing through the center of gravity of an important region having the maximum size may be displayed. Further, the case slice image of an axial cross section 39 in which the area of the important region 36 is maximized in the similar case image illustrated in FIG. 10 may be displayed as the search result.

Figure 11:
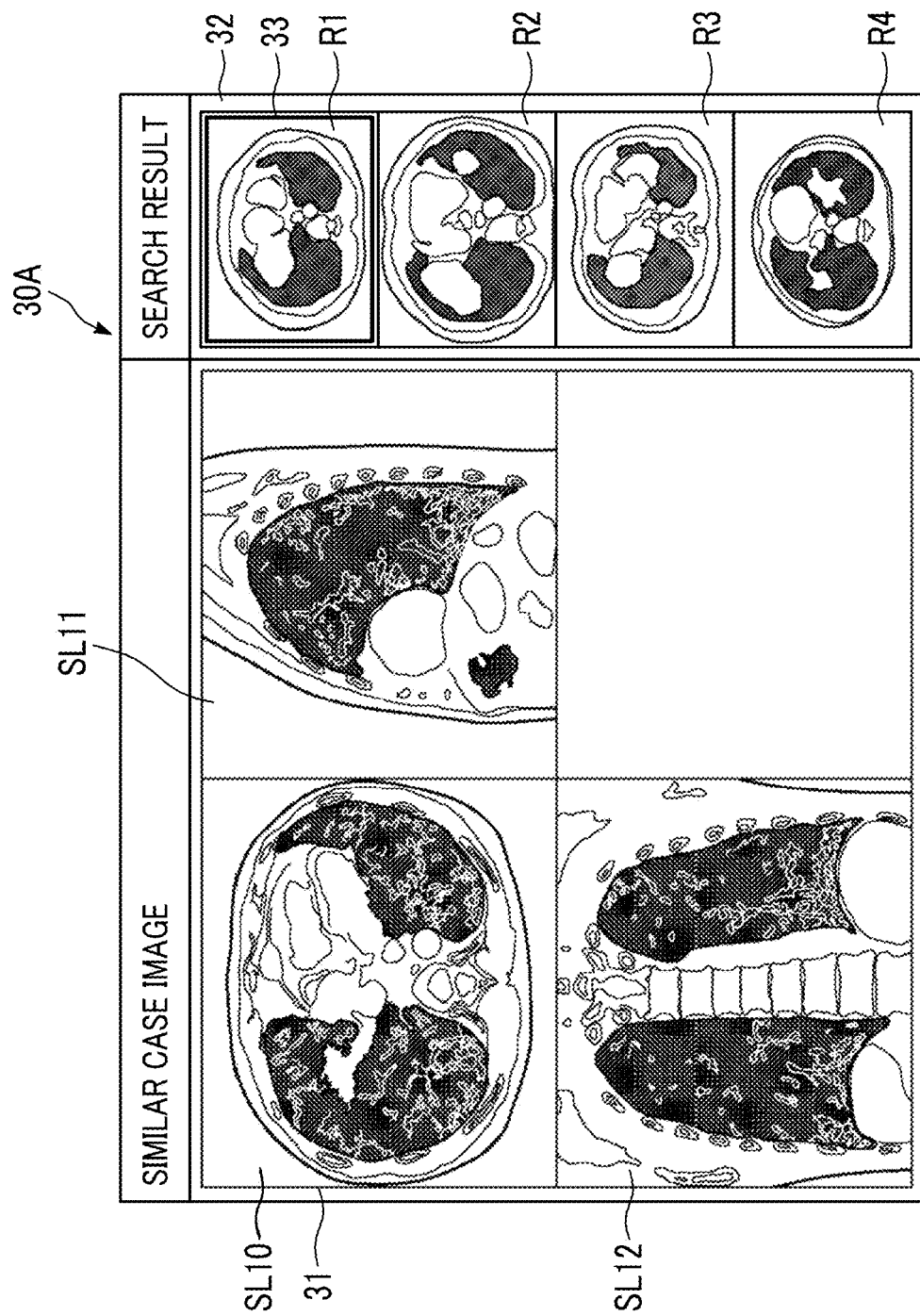
FIG. 11 is a diagram illustrating a state in which slice images of tomographic planes in three directions are displayed.

In addition, in a case in which the similar case images R1 to R4 displayed in the search result display region 32 are selected, the case slice image of the axial cross section, the case slice image of the sagittal cross section, and the case slice image of the coronal cross section in the selected similar case image may be displayed in the examination image display region 31. FIG. 11 is a diagram illustrating a state in which the case slice images of the cross sections in three directions are displayed. As illustrated in FIG. 11, assuming that the similar case image R1 among the similar case images R1 to R4 is selected on a display screen 30A, a case slice image SL10 of the axial cross section, a case slice image SL11 of the sagittal cross section, and a case slice image SL12 of the coronal cross section in the selected similar case image R1 are displayed in the examination image display region 31. Further, a frame 33 indicating that the similar case image R1 is selected is given to the similar case image R1. In addition, the letters above the examination image display region 31 are changed to "similar case image". Here, it is possible to uniquely define the cross sections in three directions passing through a certain point in a three-dimensional image. Therefore, it is possible to uniquely define the cross sections in the three directions passing through the center of gravity of the important region. Therefore, all of the case slice images SL10 to SL12 indicate the tomographic planes passing through the center of gravity of the important region.

In addition, as illustrated in FIG. 11, any one of the case slice images SL10 to SL12 of the cross sections in three directions displayed on the display screen 30A may be selected, and the case slice image of the selected tomographic plane may be switched and displayed by an operation from the input unit 15.

Figure 12:
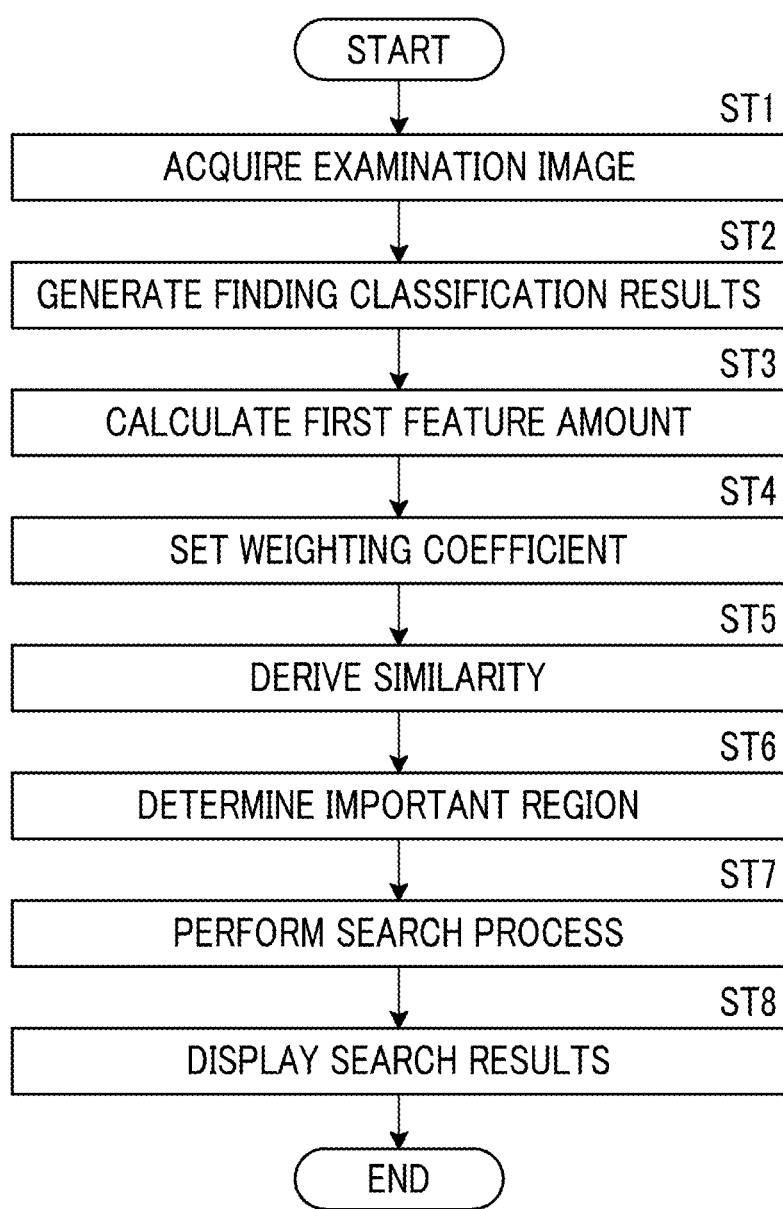
FIG. 12 is a flowchart illustrating a process performed in the first embodiment.

Next, a process performed in the first embodiment will be described. FIG. 12 is a flowchart illustrating the process performed in the first embodiment. First, the image acquisition unit 21 acquires the examination image V0 (Step ST1). The finding classification unit 22 classifies a lung region included in the examination image V0 into a plurality of types of lesion regions indicating a plurality of types of findings and generates the classification result of the findings (Step ST2). Then, the feature amount calculation unit 23 calculates the first feature amount for each finding classified in the examination image V0 (Step ST3). In addition, the weighting coefficient setting unit 24 sets the weighting coefficient Wi for each finding of the examination image V0 (Step ST4).

Then, the similarity derivation unit 25 performs a weighting operation for the first feature amount for each finding calculated in the examination image V0 and the second feature amount for each finding calculated in advance in the case image on the basis of the weighting coefficient Wi to derive the similarity between the examination image V0 and the case image (Step ST5). In addition, as described above, the similarity derivation unit 25 derives the similarities between the examination image V0 and all of the case images registered in the case database DB. Then, the region determination unit 26 determines at least one important region including the important finding for deriving the similarity in the case image (Step ST6). Further, the search unit 27 performs a search process on the basis of the similarities (Step ST7), and the display control unit 28 displays slice images including the important region as the search results on the display unit 14 (Step ST8). Then, the process ends.

In accordance with the above, according to this embodiment, a plurality of evaluation values indicating the possibility of each pixel of the examination image V0 being each of a plurality of types of findings are calculated, and each pixel of the examination image V0 is classified into at least one of the plurality of types of findings on the basis of the plurality of evaluation values. In addition, the first feature amount is calculated for each finding classified in the examination image V0. Further, the similarity between the examination image V0 and the case image is derived on the basis of the first feature amount for each finding calculated in the examination image V0 and the second feature amount for each finding calculated in advance in the case image. Furthermore, in the case image, at least one important region including the important finding for deriving the similarity is determined. A similar case image is displayed so as to include the important region. Therefore, the similar case image includes a region having features in diagnosis. As a result, according to this embodiment, in a case in which a case image similar to the examination image V0 is displayed, it is possible to quickly check the features included in the case image.

Further, in the above-described embodiment, the weighting coefficient indicating the degree of weighting, which varies depending on the size of each finding, is set for each finding classified in the examination image V0, and the weighting operation is performed for the first feature amount for each finding calculated in the examination image V0 and the second feature amount for each finding calculated in advance in the case image on the basis of the weighting coefficient to derive the similarity between the examination image V0 and the case image. However, the present disclosure is not limited thereto. An arithmetic operation may be performed for the first feature amount and the second feature amount, without using the weighting coefficient Wi, to derive the similarity. In this case, the operation may be, for example, the difference between the first feature amount and the second feature amount.

Figure 13:
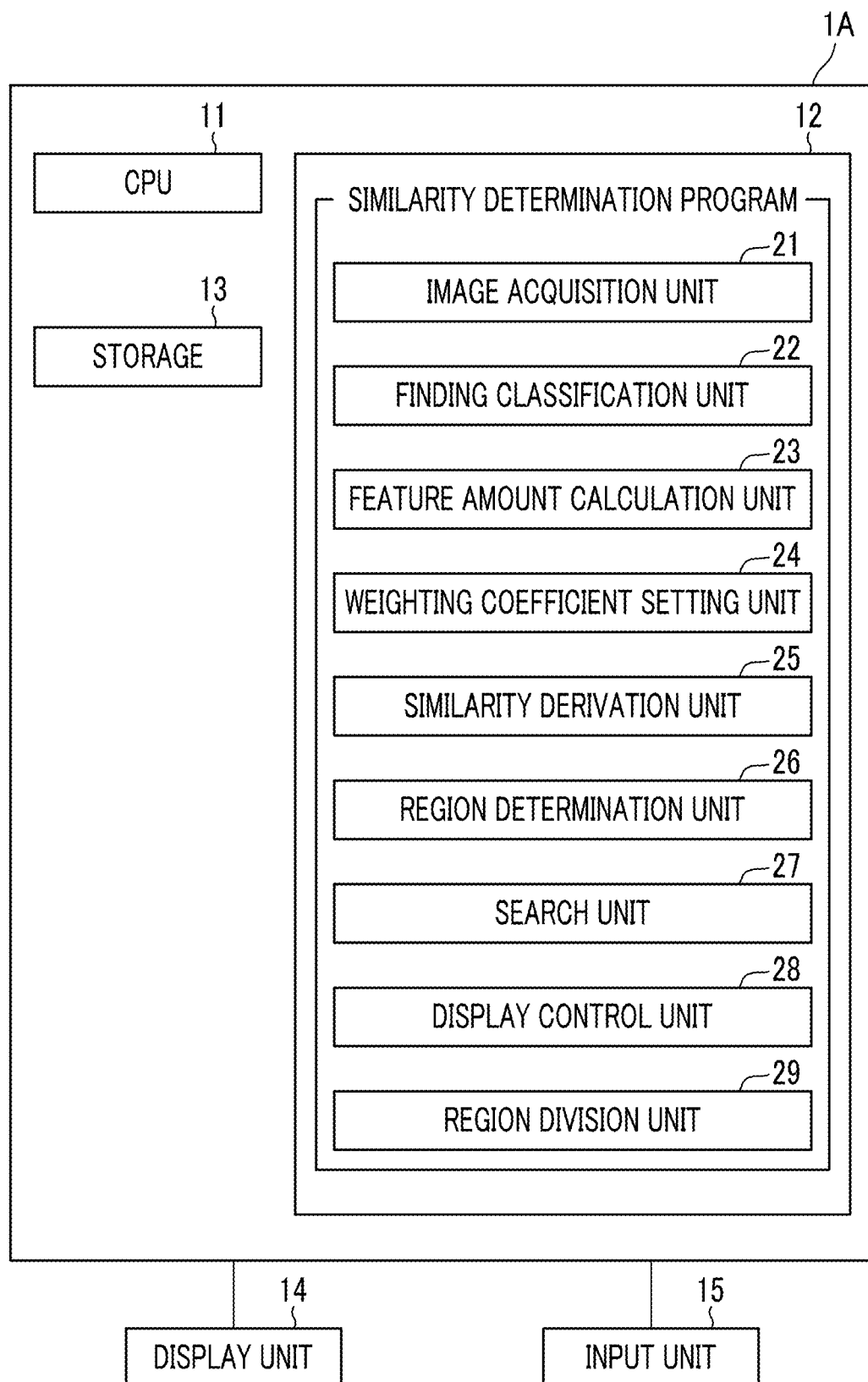
FIG. 13 is a block diagram schematically illustrating the configuration of a similarity determination apparatus according to a second embodiment.

Next, a second embodiment of the present disclosure will be described. FIG. 13 is a diagram illustrating a schematic configuration of a similarity determination apparatus according to the second embodiment of the present disclosure. Further, in FIG. 13, the same configurations as those in FIG. 2 are denoted by the same reference numerals, and the detailed description thereof will not be repeated. A similarity determination apparatus 1A according to the second embodiment is different from the similarity determination apparatus according to the first embodiment in that it further comprises a region division unit 29 that divides the lung region of the examination image V0 into a plurality of regions.

Figure 14:
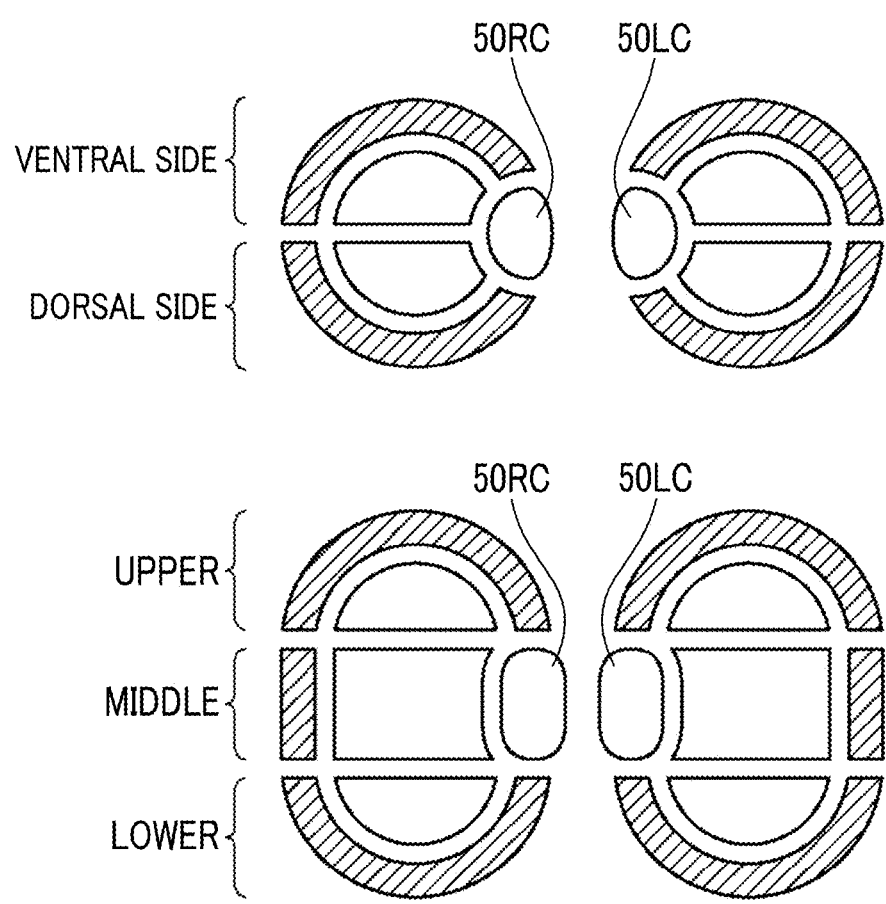
FIG. 14 is a diagram illustrating the division of a lung region.

The region division unit 29 divides the lung region into a plurality of regions. FIG. 14 is a diagram illustrating the division of the lung region. As illustrated in FIG. 14, the region division unit 29 divides the left and right lung regions into a left central region 50LC, a right central region 50RC, and other regions. Then, the region other than the central region is further divided into three regions of upper, middle, and lower regions, intermediate and outer regions, and ventral and dorsal sides. In FIG. 14, the outer region is hatched. In the second embodiment, the region division unit 29 divides each of the left and right lung regions into 13 regions.

In the second embodiment, the feature amount calculation unit 23 calculates the first feature amount for each finding classified in the examination image V0 for each divided region. The similarity derivation unit 25 derives the similarity between the examination image V0 and the case image for each divided region. In addition, the similarity for each region is referred to as a region similarity. The region determination unit 26 determines the important region on the basis of the region similarity. Specifically, among the region similarities for each of the 13 regions divided by the region division unit 29, a region having the maximum region similarity is determined as the important region.

Figure 15:
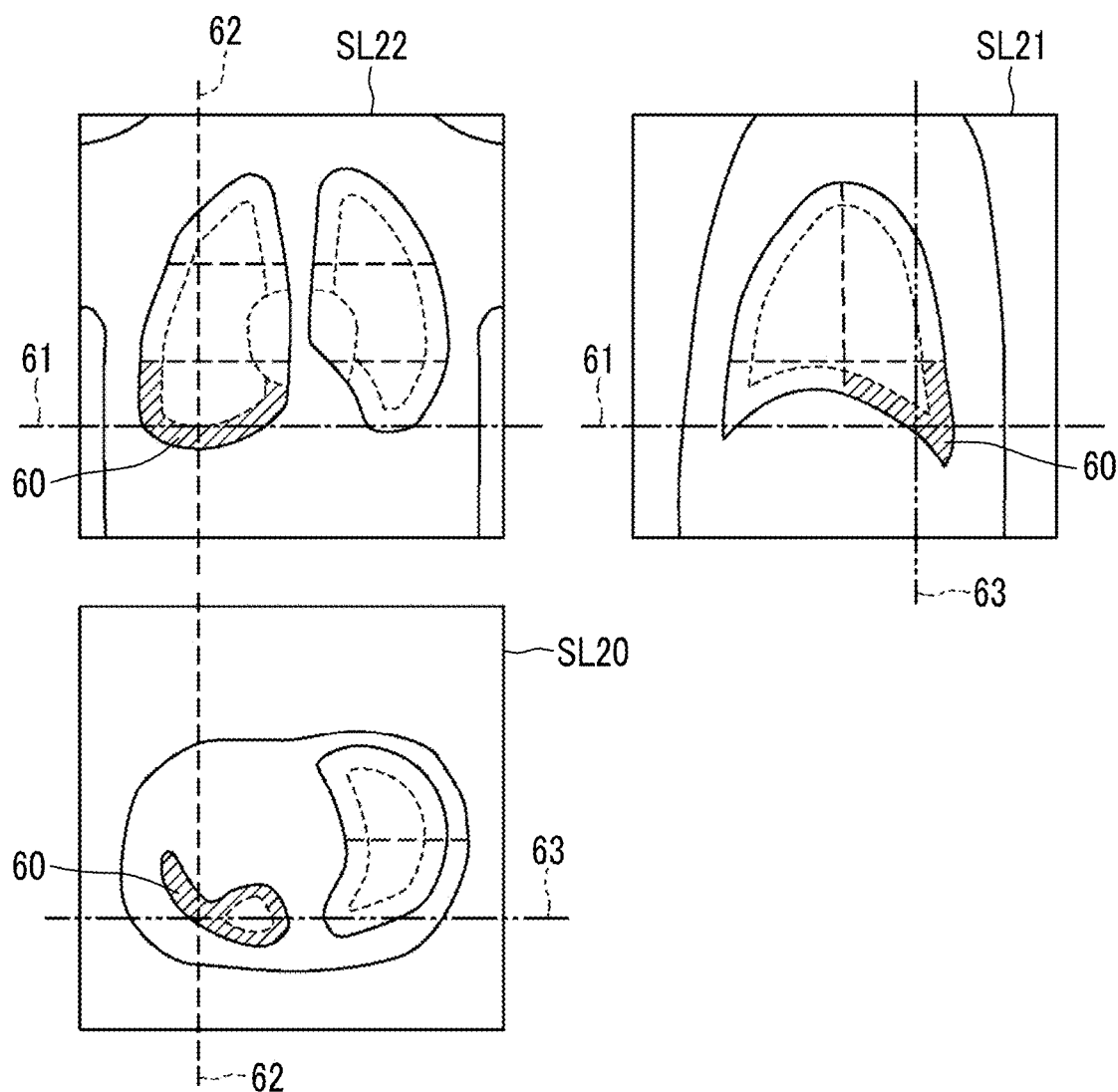
FIG. 15 is a diagram illustrating a state in which tomographic images in the directions of three axes are displayed.

FIG. 15 is a diagram illustrating the determination of the important region in the second embodiment. In addition, in FIG. 15, an important region 60 is hatched in each of a case slice image SL20 of the axial cross section, a case slice image SL21 of the sagittal cross section, and a case slice image SL22 of the coronal cross section. Further, in FIG. 15, the boundary between the divided regions in the lung region is represented by a dashed line. Furthermore, in FIG. 15, the axial cross section is represented by a one-dot chain line 61, the sagittal cross section is represented by a long dashed line 62, and the coronal cross section is represented by a two-dot chain line 63.

In addition, in the second embodiment, the similarity derivation unit 25 derives the similarity between the examination image V0 and the case image on the basis of the region similarities. For example, the similarity between the examination image V0 and the case image is derived on the basis of the weighted addition value of the region similarities, the maximum value of the region similarities, the average value of the region similarities, and the like.

The display control unit 28 displays the slice image including the important region as the search result on the display unit 14. In the second embodiment, similarly to the first embodiment, the slice image of the axial cross section 38 passing through the center of gravity 37 of the important region 36 in the similar case image or the slice image in which the area of the important region is maximized may be displayed as the search result. However, the present disclosure is not limited thereto.

Figure 16:
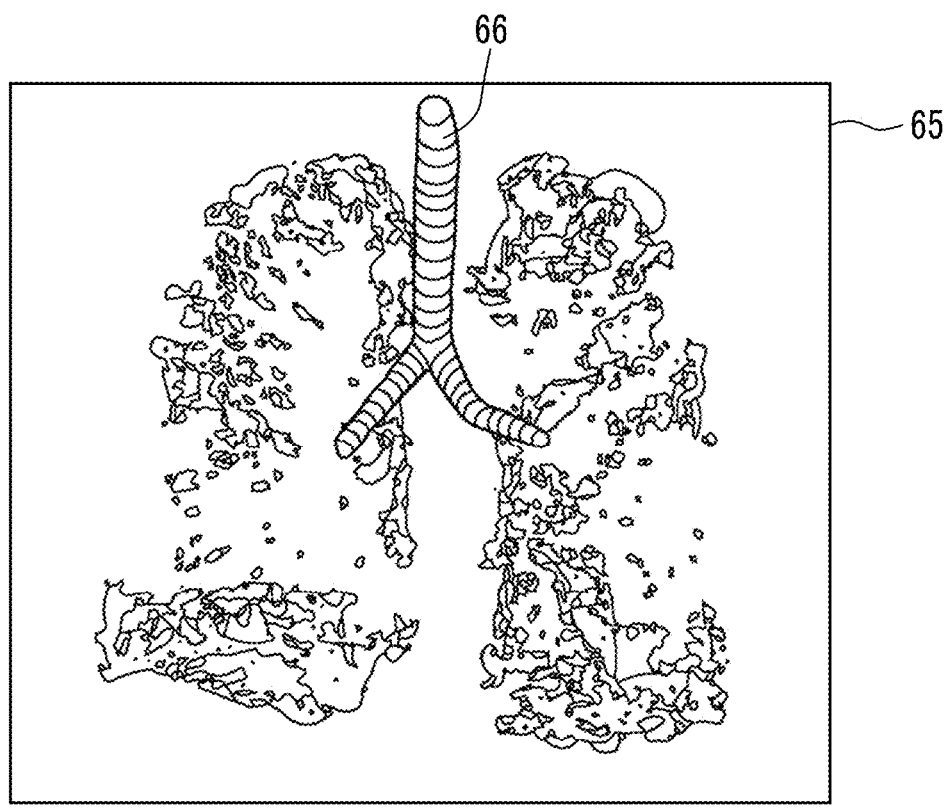
FIG. 16 is a diagram illustrating a three-dimensional image in which an important region is highlighted.

Further, in the first and second embodiments, the similar case image may be displayed as a three-dimensional image. In this case, the three-dimensional image in which the important region is highlighted may be displayed. FIG. 16 is a diagram illustrating a three-dimensional image in which an important region is highlighted. In a three-dimensional image 65 illustrated in FIG. 16, only the important region is opaque and the other regions are transparent. In FIG. 16, a bronchus 66 is opaque in order to clarify the positional relationship in the lung. Further, in addition to the three-dimensional image illustrated in FIG. 16, the case slice image of the tomographic plane including the important region in the similar case image may be displayed. In this case, the case slice images of all of the axial cross section, the sagittal cross section, and the coronal cross section may be displayed, or the case slice image of any one of the cross sections may be displayed.

Further, in the above-described embodiments, the tomographic image of the examination image V0 is displayed on the display unit 14. However, the present disclosure is not limited thereto. The finding classification unit 22 may generate a mapping image of the examination image V0, and the tomographic image of the mapping image may be displayed on the display unit 14.

Figure 17:
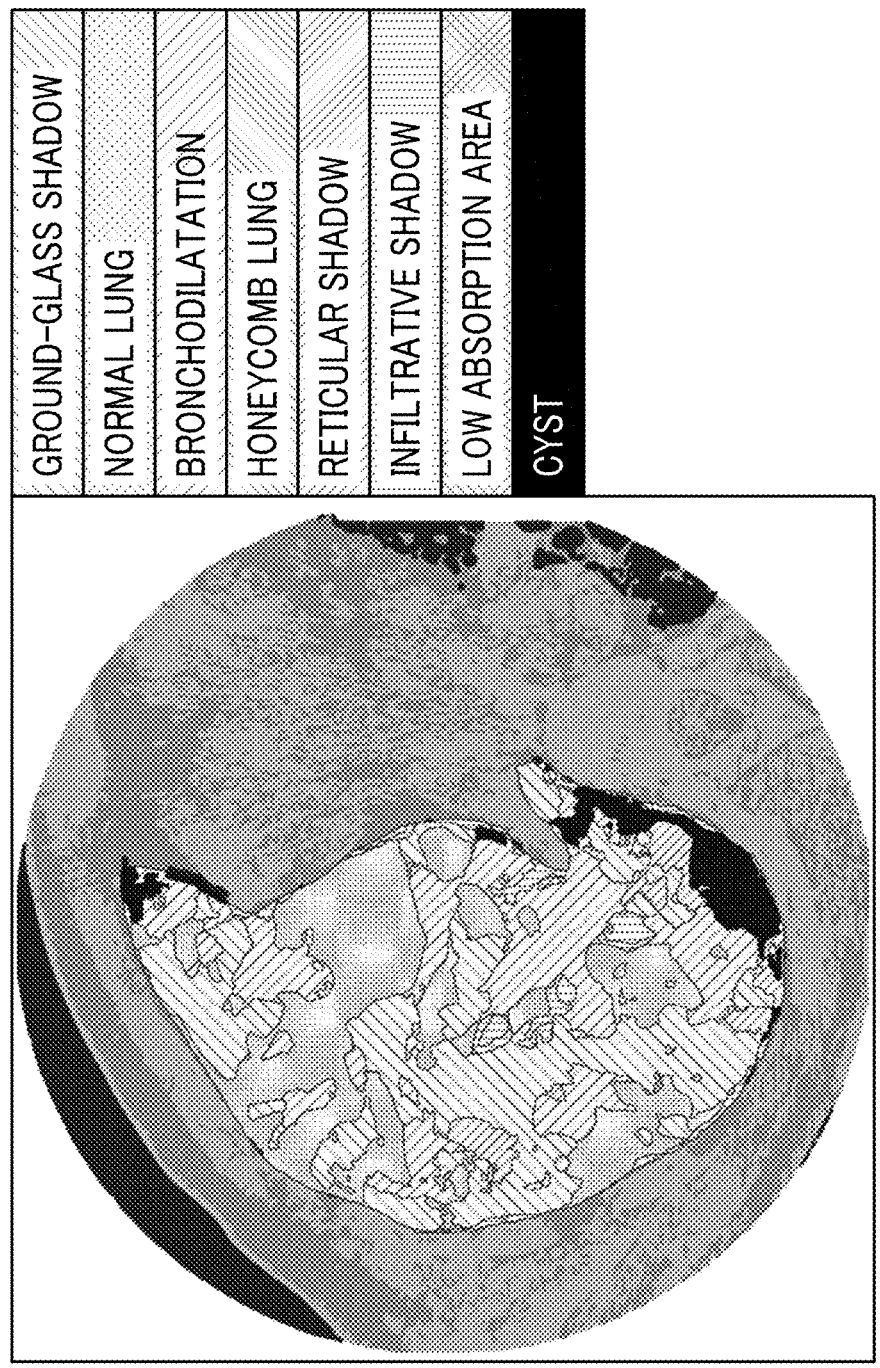
FIG. 17 is a diagram illustrating a mapping image to which colors corresponding to classifications are assigned.

That is, colors may be assigned to each classification region on the basis of the result of the finding classification process of the finding classification unit 22 to generate a mapping image, and the generated mapping image may be displayed. Specifically, the finding classification unit 22 assigns the same color to the pixels classified into the same finding for all of the pixels in a three-dimensional space classified into any of the plurality of types of findings to generate a three-dimensional mapping image. FIG. 17 is a diagram illustrating one tomographic plane of the mapping image in which colors corresponding to a plurality of types of classifications are assigned. In addition, FIG. 17 illustrates the mapping image in a case in which the pixels are classified into eight types of findings, that is, a ground-glass shadow, a normal lung, bronchodilatation, a honeycomb lung, a reticular shadow, an infiltrative shadow, a low absorption area, and a cyst for simplicity of description. Further, FIG. 17 illustrates only the mapping image of one lung.

Further, in each of the above-described embodiments, a plurality of evaluation values indicating the possibility of each pixel of the examination image V0 being each of a plurality of types of findings are calculated for each pixel, and each pixel of the examination image V0 is classified into at least one of the plurality of types of findings on the basis of the plurality of evaluation values. However, a finding classification method is not limited to the method using the evaluation values.

In addition, in each of the above-described embodiments, the case database DB is stored in the image storage server 3. However, the case database DB may be stored in the storage 13.

Further, in each of the above-described embodiments, the examination image is registered in the case database DB. However, images other than the examination image may be registered as registration target images in the case database.

In each of the above-described embodiments, for example, the following various processors can be used as the hardware structure of processing units performing various processes, such as the image acquisition unit 21, the finding classification unit 22, the feature amount calculation unit 23, the weighting coefficient setting unit 24, the similarity derivation unit 25, the region determination unit 26, the search unit 27, the display control unit 28, and the region division unit 29. The various processors include a CPU which is a general-purpose processor executing software (program) to function as various processing units as described above, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system on chip (SoC). In accordance with the above, various processing units are configured by using one or more of the various processors as a hardware structure.

Furthermore, specifically, an electric circuit (circuitry) obtained by combining circuit elements, such as semiconductor elements, can be used as the hardware structure of the various processors.

What is claimed is:

1. A similarity determination apparatus that determines a similarity between a first three-dimensional medical image and a second three-dimensional medical image, the similarity determination apparatus comprising at least one processor, wherein the processor is configured to:
   classify each pixel of the first medical image into at least one of a plurality of types of findings;
   calculate a first feature amount for each finding classified in the first medical image;
   derive the similarity between the first medical image and the second medical image on the basis of the first feature amount for each finding calculated in the first medical image and a second feature amount for each finding calculated in the second medical image; and
   determine at least one important region including an important finding for deriving the similarity in the second medical image.

2. The similarity determination apparatus according to claim 1, wherein the processor is configured to:
   set a weighting coefficient indicating a degree of weighting, which varies depending on a size of each finding, for each finding classified in the first medical image, and
   determine the important region on the basis of the weighting coefficient.

3. The similarity determination apparatus according to claim 1, wherein the processor is configured to determine the important region on the basis of a similarity for each finding based on the first feature amount for each finding and the second feature amount for each finding.

4. The similarity determination apparatus according to claim 1, wherein the processor is configured to:
   divide a target region of the first medical image into a plurality of regions,
   calculate the first feature amount for each finding classified in the first medical image in each of the divided regions,
   derive a region similarity between the first medical image and the second medical image for each of the divided regions and derive the similarity between the first medical image and the second medical image on the basis of a plurality of the region similarities, and
   determine the important region on the basis of the region similarities.

5. The similarity determination apparatus according to claim 1, wherein the processor is configured to search for the second medical image similar to the first medical image as a similar medical image on the basis of similarities between the first medical image and a plurality of second medical images with reference to a case database in which the plurality of second medical images are registered and a second feature amount for each of the plurality of second medical images is registered so as to be associated with each of the plurality of second medical images.

6. The similarity determination apparatus according to claim 5, wherein the processor is configured to display a slice image including the important region in the similar medical image as a search result on a display.

7. The similarity determination apparatus according to claim 5, wherein the processor is configured to display a slice image which passes through a center of gravity of one important region in the similar medical image as a search result on the display.

8. The similarity determination apparatus according to claim 5, wherein the processor is configured to display a slice image in which an area of one important region is maximized in the similar medical image as a search result on the display.

9. The similarity determination apparatus according to claim 5, wherein the processor is configured to three-dimensionally display the similar medical image in which the important region is highlighted as a search result on a display.

10. A similarity determination method that determines a similarity between a first three-dimensional medical image and a second three-dimensional medical image, the similarity determination method comprising:
    classifying each pixel of the first medical image into at least one of a plurality of types of findings;
    calculating a first feature amount for each finding classified in the first medical image;
    deriving the similarity between the first medical image and the second medical image on the basis of the first feature amount for each finding calculated in the first medical image and a second feature amount for each finding calculated in the second medical image; and
    determining at least one important region including an important finding for deriving the similarity in the second medical image.

11. A non-transitory computer-readable storage medium that stores a similarity determination program that causes a computer to perform a process of determining a similarity between a first three-dimensional medical image and a second three-dimensional medical image, the similarity determination program causing the computer to perform:
    a step of classifying each pixel of the first medical image into at least one of a plurality of types of findings;
    a step of calculating a first feature amount for each finding classified in the first medical image;
    a step of deriving the similarity between the first medical image and the second medical image on the basis of the first feature amount for each finding calculated in the first medical image and a second feature amount for each finding calculated in the second medical image; and
    a step of determining at least one important region including an important finding for deriving the similarity in the second medical image.

* * * * *